United States Patent [19]
Ess

[11] Patent Number: 5,782,236
[45] Date of Patent: Jul. 21, 1998

[54] VENTILATOR TUBE RETAINING DEVICE FOR ENDOTRACHEAL TUBE OR TRACHEOSTOMY

[76] Inventor: Steven M. Ess, 6864 Minnick Rd., Lockport, N.Y. 14094

[21] Appl. No.: 695,372

[22] Filed: Aug. 9, 1996

[51] Int. Cl.⁶ .................................................. A61M 16/00
[52] U.S. Cl. ...................... 128/207.17; 128/DIG. 26; 128/912; 128/207.14; 24/339
[58] Field of Search ..................... 128/207.17, 207.14, 128/207.18, 911, 912, DIG. 26, 200.26; 138/120, 109, 155; 285/114; 24/543, 339, 17 B

[56] References Cited

U.S. PATENT DOCUMENTS

| | | | |
|---|---|---|---|
| 744,408 | 11/1903 | Rosenthal | 138/120 |
| 770,982 | 9/1904 | Plassmann | 285/114 |
| 874,378 | 12/1907 | Allen | 285/114 |
| 1,310,627 | 7/1919 | McEvilly | 285/114 |
| 1,434,532 | 11/1922 | Davala | 24/339 |
| 1,989,823 | 2/1935 | Raabe | 24/339 |
| 2,191,782 | 2/1940 | Valane | 24/339 |
| 2,864,378 | 12/1958 | Schneller et al. | 285/114 |
| 3,206,086 | 9/1965 | Duffney | 24/339 |
| 3,249,370 | 5/1966 | Brogden | 285/114 |
| 3,987,798 | 10/1976 | McGinnis | 128/207.17 |
| 4,249,529 | 2/1981 | Nestor et al. | 128/207.17 |
| 4,351,331 | 9/1982 | Gereg | 128/207.17 |
| 4,732,147 | 3/1988 | Fuller | 128/207.18 |
| 4,774,944 | 10/1988 | Mischinski | 128/207.17 |
| 5,069,206 | 12/1991 | Crosbie | 128/207.17 |
| 5,076,269 | 12/1991 | Austin | 128/207.17 |
| 5,117,818 | 6/1992 | Palfy | 128/204.11 |
| 5,295,480 | 3/1994 | Zemo | 128/207.17 |
| 5,320,097 | 6/1994 | Clemens et al. | 128/207.17 |
| 5,357,952 | 10/1994 | Schuster et al. | 128/207.17 |
| 5,368,024 | 11/1994 | Jones | 128/207.17 |
| 5,402,776 | 4/1995 | Islava | 128/207.17 |
| 5,485,837 | 1/1996 | Solesbee | 128/207.17 |
| 5,501,216 | 3/1996 | Byrd | 128/207.17 |
| 5,507,533 | 4/1996 | Mumma | 285/114 |
| 5,551,421 | 9/1996 | Noureldin et al. | 128/207.17 |
| 5,697,129 | 12/1997 | Newville | 24/339 |
| 5,703,330 | 12/1997 | Kujawski | 24/339 |

*Primary Examiner*—Mickey Yu
*Assistant Examiner*—William J. Deane, Jr.
*Attorney, Agent, or Firm*—Trapani & Molldrem

[57] ABSTRACT

A retaining clamp device holds a tubular air fitting to an endotracheal tube or tracheostomy, e.g., disposed on the neck of the patient. A C-shaped clamp member is formed of a resilient semi-rigid plastic and has an inside diameter that fits snugly over the air fitting, with one or more legs connected to the C-shaped clamp member. The legs have slots at their free ends to fasten the clamp member to said to the flange of the endotracheal tube assembly, e.g., using the Velcro strips that hold the flange to a neck collar. The legs can include left and right leg members that extend from opposite sides of the C-shaped clamp member. The attendant or patient can snap the C-shaped member on or off the fitting of a ventilator tube, moving the C-shaped member to the side.

6 Claims, 2 Drawing Sheets

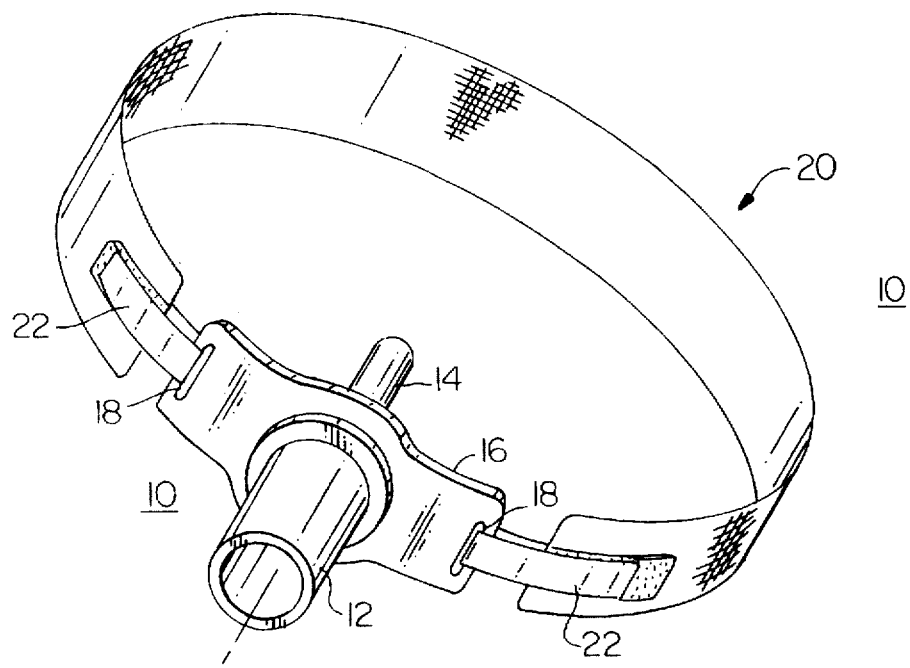
FIG.1
Prior Art
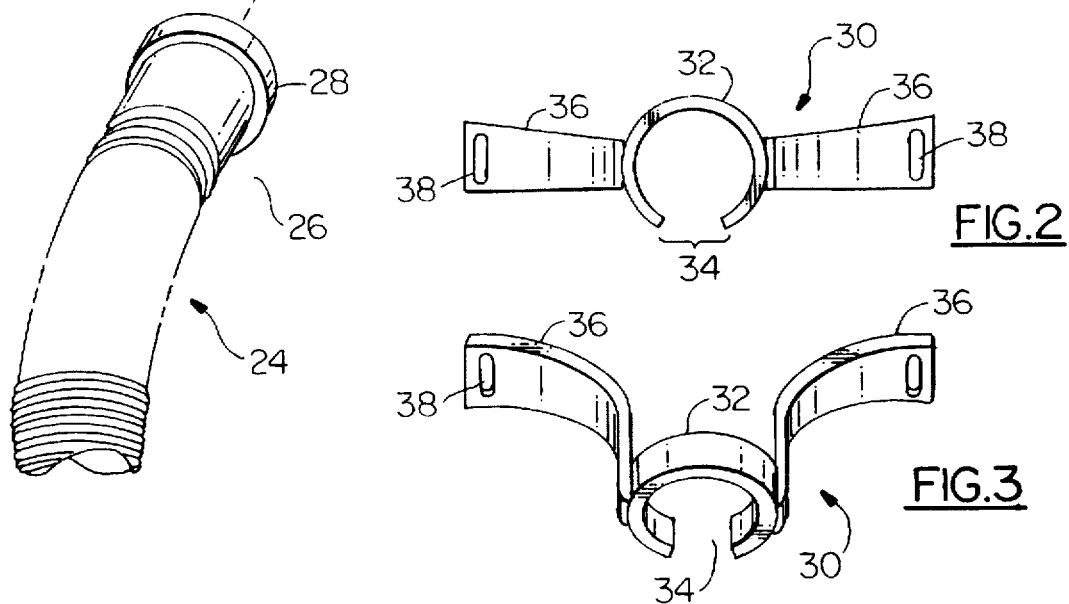
FIG.2
FIG.3

VENTILATOR TUBE RETAINING DEVICE FOR ENDOTRACHEAL TUBE OR TRACHEOSTOMY

BACKGROUND OF THE INVENTION

This invention relates generally to medical and surgical devices, and is more particularly concerned with a device for retaining a hose or tube for breathing apparatus onto an endotracheal tube or tracheostomy tube of a patient. The invention is more specifically directed to a device for releasably securing a ventilator tube to a tracheostomy tube or a endotracheal tube. The invention is further concerned with a retaining device which prevents inadvertent decoupling or disconnecting of the ventilator tube from the patient.

The medical community is now recognizing the importance to breathing impaired patients of securing the ventilator circuit to the endotracheal tube or to the tracheostomy tube. Respiratory therapists working with both acute and chronic ventilator patients, with either a tracheostomy tube or an oral/nasal endotracheal tube, have observed that such patients oftentimes find themselves disconnected from the ventilator circuit. This may come about simply due to motion when the patients reposition themselves, or when the nurse repositions them. Other common reasons for disconnection may be strong, persistent coughing which allows for secretions to lubricate the connection site and create a loose connection, or disorientation of the patient, i.e., where the patient is turning in bed or pulling on lines and catheters that may cause the circuit to become disconnected. These examples are rather prevalent in a critical care setting, and in a chronic ventilator care rehabilitation setting. However, these problems are also found with home-care patients. Patients who become ventilator-dependent and are living at home generally have at least some limited mobility. Some of these home-care patients require connection to the ventilator only at night while sleeping, and in that case rolling in bed or movement during sleep, e.g., if the patient experiences troubled dreams, can result in disconnection from the ventilator tube. Those who are quadriplegic, i.e., neuromuscularly impaired, can find themselves disconnected from the ventilator tube and with no means to reposition the tube by themselves. In most circumstances an attendant, nurse or caregiver is present. However, if the patient becomes disconnected while the caregiver has stepped away momentarily, even for the short time it takes to check the mail or prepare medication, the patient can become tachypneic and cyanotic, risking injury.

In the case of higher pressure ventilation, the pressure itself may cause the disconnection. For example, pressure levels may be 15 to 20 cm ($H_2O$), with pressure control levels in the range of 30 to 40 cm ($H_2O$). These high pressures alone may overcome the friction or press fit that is usually used for a suction-trach connect or wye-trach connect. These connections may become disconnected just from the pressures employed. At somewhat lower pressures, the ventilator connects may come off when the patient coughs. Many patients have large necks or jowls that can interfere with the ventilator-trach connect.

Because of these and other problems, the medical and health care professions have needed a simple and reliable means to secure the ventilator tube to the tracheostomy or endotracheal tube, but also require that this securing means not interfere with placement and removal of the ventilator when the ventilator tube needs to be changed. It is also desirable to give the patient a calming sense of security, knowing that the ventilator tube is not going to become disconnected.

At the present time, it is the practice to use one or two rubber bands to secure the ventilator connection to the endotracheal tube or tracheostomy. These do little more than increase the friction fit a small amount. In the case of a straight connection, there is nothing to secure the rubber bands onto, and the ventilator can still become disconnected.

A retention device that attempts to address some of these problems is described in U.S. Pat. No. 5,357,952 (Shuster et al.). In that case, the medical tube retention device includes a band or strap that wraps around the ventilator connector and is fastened by Velcro patches to the collar that hold the tracheostomy flange against the patient's throat. Because a wrap is employed, it is necessary for the ventilator connect to be L-shaped. Also, because the straps connect the ventilator connect to the collar rather than to the tracheostomy flange, this arrangement places pressure against the patient's throat, and can cause noticeable discomfort.

Some other ventilator tube retention devices are described, e.g., in Islava U.S. Pat. No. 5,402,776; Crosbie U.S. Pat. No. 5,069,206; and Clemens et al. U.S. Pat. No. 5,320,097. The devices shown in these patents involve multiple-part clamps that can be difficult for the patient or caregiver to manipulate, and would be somewhat impractical for solving the problems described above.

OBJECTS AND SUMMARY OF THE INVENTION

It is an important object of the present invention to provide a ventilator tube retaining device that overcomes the drawbacks of the prior art as mentioned just above.

It is a more specific object to provide a retaining device that facilitates securing the ventilator to the patient, and better facilitates the management of patients with either tracheostomy tubes or oral/nasal endotracheal tubes.

It is a further object to provide a retaining device that snaps onto either the closed suction adaptor, a 90° elbow, or a wye connector, and which secures itself using the existing tracheostomy tube holder or endotracheal tube holder, e.g., with existing Velcro or similar straps.

It is a yet further object to facilitate the easy placement or removal of the retaining device itself, and to allow for changing of the ventilator circuit at regular intervals without having to undo the Velcro straps that secure the tracheostomy or endotracheal tube.

A still further object is to permit the ventilator circuit to be disconnected quickly in an emergency, such as to remove a mucus plug or for resuscitator bag ventilation.

In accordance with an aspect of the present invention, a retaining device yieldably retains a tubular air fitting to an endotracheal (including tracheostomy) tube, and especially the type of tube having a flange with left and right slots, and in which a collar device is disposed on the neck of the patient with left and right ribbons, e.g., Velcro straps, affixed to the collar device that pass through the left and right slots of the flange to hold the flange and endotracheal tube in place on said patient. In many favorable embodiments of the retaining device, a C-shaped clamp member is formed of a resilient semi-rigid material and has an inside diameter to fit snugly over the air fitting. A leg or legs joined to the C-shaped clamp member receive the left and said right ribbons, respectively, thus securing said retaining device to the flange. The retaining device can have left and right leg members that extend from opposite sides of the C-shaped clamp member. The C-shaped clamp member and the leg members are favorably unitarily formed of a resilient plastic resin. The C-shaped clamp member has its gap dimensioned to permit the C-shaped clamp member to spread at the gap over said air fitting to snap on or snap off. This means that the clamp member can be pushed on and off to the side, so that the ventilator circuit can be quickly and easily secured and removed. The health care provider can do this using only two fingers of one hand. The yieldable clamp member also permits the ventilator circuit to be pulled off with a firm tug, where emergency removal is needed.

The retaining device can take other forms. For example, two tubes or connectors can be joined using a device which employs a first C-shaped clamp member, formed of a resilient, semi-rigid material and having an inside diameter to fit snugly over an air fitting, a second retaining member that removably attaches to another tubular air conduit or connector, and a leg or similar member joins the C-shaped clamp member to the second retaining member. The second retaining member can itself be a C-shaped clamp member likewise formed of a resilient semi-rigid material and having an inside diameter to fit snugly over the other air conduit or connector. In that case the leg member holds the first and second C-shaped clamp members generally in axial alignment. Another possible embodiment can employ first and second legs situated oppositely on the C-shaped clamp member, and first and second retaining fingers directed inwardly at free ends of said first and second legs. Preferably these first and second legs extend parallel to one another.

The above and many other objects, features, and advantages of this invention will become more fully appreciated from the ensuing detailed description of selected preferred embodiments, which should be considered in conjunction with the accompanying Drawing.

BRIEF DESCRIPTION OF THE DRAWING

FIG. 1 is a perspective view of a tracheostomy tube and holder, and a ventilator tube fitting, according to the state of the art.

FIGS. 2 and 3 are a front view and a perspective view, respectively, of a ventilator tube retaining clamp according to an embodiment of the present invention.

DETAILED DESCRIPTION OF THE PREFERRED EMBODIMENTS

Figure 4:
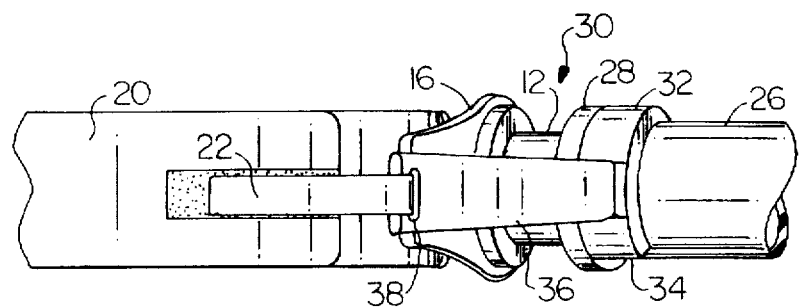
FIG. 4 is a side view of the tracheostomy tube and ventilator tube held in place by the retaining clamp of this embodiment.

With reference now to the Drawing, FIG. 1 shows a tracheostomy tube assembly 10 of the type that can be fitted to a tracheostomy patient. The assembly 10 has an external tube 12 and an internal tube 14 which passes through a stoma in the patient's throat into the trachea or windpipe. A buckle-shaped flange 16 positions and holds the tube assembly in place on the patient. There are left and right slots 18, 18 at the sides of the flange 16. A collar 20 encircles the patient's neck to anchor the tube assembly 10 to the patient.

There are Velcro straps or ribbons 22, 22 on the left and right ends of the collar, and these pass through the flange slots 18, 18 as shown and are secured to the provided Velcro patches on the collar. A ventilator tube 24 is used to supply air to the patient through the tracheostomy external tube 12, or to exhaust expiratory breath from the patient. The ventilator tube can include means (not shown here) for injecting medication or moisture. At the end of the tube 24 is a round fitting 26 that is press-fitted onto the external tube 12. At the extreme end of the fitting is a flange or annular ridge 28. It is common practice among respiratory care practitioners to use a rubber band or a cloth or plastic strip to tie the ventilator tube in place. This usually entails tying rubber band or strip at one end to the ventilator fitting 26 and at the other end to the collar 20. The result of this is that the fitting 26 is pulled against the patient's neck, causing pressure and discomfort. Also, the rubber bands and strips are sometimes difficult to secure in place, and often do not lend much holding power above that of the friction fit of the fitting 26 onto the external tube 12.

A ventilator securing retaining clamp device 30 according to one embodiment of this invention is shown in FIGS. 2 and 3. The device 30 is dimensioned to fit onto the flange 16 and to snap fit over the ventilator fitting 26. The clamp device 30 is formed of a resilient, flexible material, such as a semi-rigid plastic resin. A C-shaped clamp member 32 has an inner smooth surface and an inner diameter dimensioned to fit snugly onto the generally cylindrical outside surface of the ventilator fitting 26. The clamp member has a gap 34, here shown at the lower side, of about 60 degrees of arc. The gap 34 spreads to accommodate the fitting 26 when the clamp member 32 is snapped on and off. There are left and right legs 36, 36 that extend from the left and right side of the C-shaped clamp member 32, and have elongated slots 38, 38 at their free ends. The legs 36 can be affixed onto, or unitarily formed with the C-shaped member 32. The slots 38, 38 align approximately with the slots 18, 18 of the flange, so that the clamp device 30 can be secured to the flange 16 by means of the Velcro strips 22, 22.

The clamp device 30 is installed as shown in FIG. 4, with the collar 20 holding the flange 16 of the tracheostomy tube assembly 10 in place on the neck of the patient. The ventilator tube fitting 36 is fitted in place over the external tube 12, and the clamp device is installed as shown, with the legs secured by the Velcro straps 22, 22 to the flange 16, and with the C-shaped member 32 being snapped in place onto the fitting 26 against the annular flange 28 The clamp device 30 assists holding the ventilator tube in place in two ways: (a) the pressure of the interference fit of the C-shaped member 32 on the fitting 36 increases the friction between the fitting and the external tube 12, and (b) the member 32 physically blocks the flange 28 from axial movement away from the patent's throat.

Figure 5:
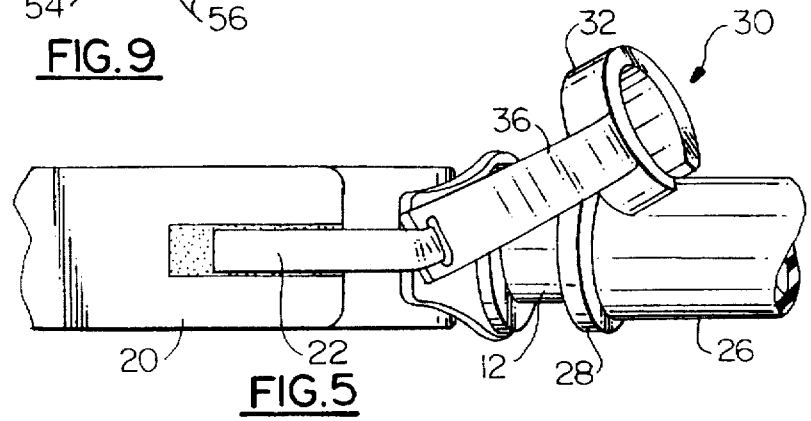
FIG. 5 is a side view as in FIG. 4, but showing the retaining clamp snapped off to one side to release or install the ventilator tube.

The snap action of this clamp device 30 can be explained with reference to FIG. 5, which shows the same basic elements as shown if FIG. 4, but with the C-shaped member 32 pushed off the fitting 26 (upward in this view). As mentioned before, the gap 34 and the flexibility of the material of the member 32 permits the member 32 to flex and spread to pass around the fitting 26. The C-shaped member 32 snaps on and off the fitting 28, from the side. This can be accomplished by the respiratory care practitioner, or by the patient himself or herself, using only one hand. The C-shaped member is also sufficiently yieldable to permit the fitting 26 to be pulled directly off, through the member 32, if the practitioner, or patient, pulls sharply and firmly outward. This feature allows the respiratory circuit to be disconnected quickly, i.e., pulled out, in an emergency situation.

Figures 6, 7:
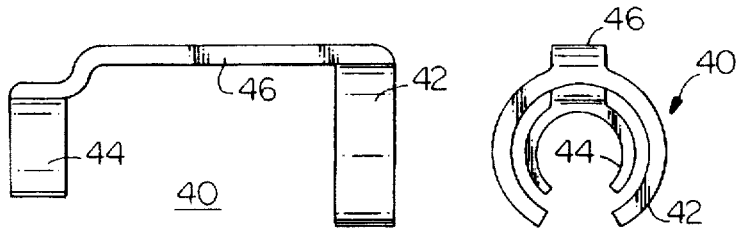
FIGS. 6 and 7 are side and front views, respectively, of a retaining clamp device of a second embodiment.

An alternative embodiment of the clamp device of this invention is shown if FIGS. 6 and 7. There a retaining device 40 is designed for joining two tubing connectors in axial alignment. This retaining device can be used with a wye connect or other tubes between the patient and the respirator apparatus. It should be appreciated that an unintentional disconnection of any respiratory equipment tubing could endanger the patient.

As shown in FIGS. 6 and 7, the retaining device 40 has a first C-shaped clamp member 42 that is similar to the member 32 as previously described. There is also a second C-shaped clamp member 44, here of a different diameter and adapted to fit onto a smaller-diameter conduit. A leg member 46 joins the two C-shaped members 42, 44. The leg member 46 includes an offset 47 so that the two C-shaped members are generally in axial alignment.

Figure 8:
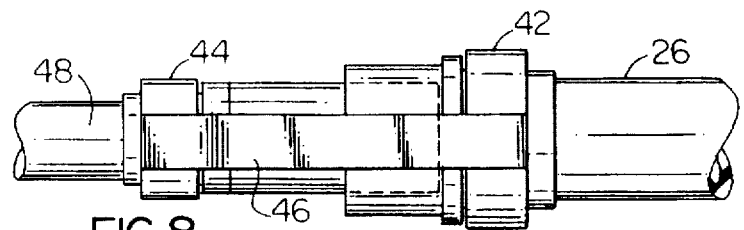
FIG. 8 is a side view showing the retaining clamp device of the second embodiment holding two tubular ventilator members together.

As shown in FIG. 8, the connector 26 can be joined to another ventilator conduit 48 using this retaining device 40. Here the first C-shaped member 42 is snap-fitted onto the fitting 26, and the other C-shaped member 44 is snap-fitted onto the other conduit 48. The device 40 keeps these two tubular members 26, 48 from being inadvertently pulled apart, but will permit them to be separated when that is intended. The retaining device can be easily snapped off to the side to permit separation of the ventilator tubes when required.

Figure 10:
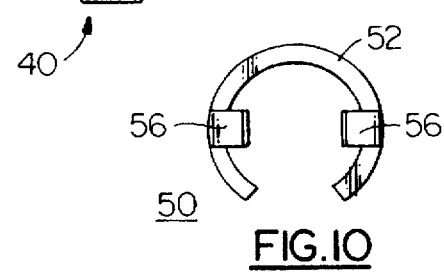
FIGS. 9 and 10 are a perspective view and an end view, respectively, of a retaining device according to a third embodiment.
Figure 9:
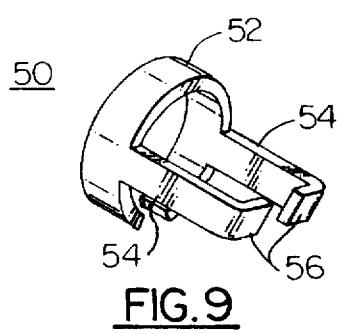

A further embodiment of the clamp or retaining device 50 of this invention is shown in FIGS. 9 and 10. Here the clamp device 50 has a C-shaped, flexibly resilient clamp member 52, similar to that as generally described above, with a pair of parallel legs 54, 54 extending axially from opposite sides of the clamp member 52. There are inwardly directed retaining fingers 56, 56 at the free ends of these legs 54, 54. This can be employed in a number of situations where a ventilator tube or fitting is to be secured. This embodiment is illustrative of only one of the wide range of possible embodiments that employ the main principles of this invention.

While the invention has been described in detail with reference to a few selected embodiments, it should be recognized that the invention is not limited to those precise embodiments. Rather, many modifications and variations would present themselves to persons skilled in the art without departure from the scope and spirit of this invention, as defined in the appended claims.

I claim:

1. A retaining device for yieldably retaining a tubular air fitting to an endotracheal tube or tracheostomy tube, said retaining device having a flange with left and right slots, collar means adapted to be disposed on a patient's neck; left and right ribbons affixed to said collar means and passing through the left and right slots of said flange to hold the flange and endotracheal tube or tracheostomy tube in place on a patient; the retaining device comprising:

a C-shaped clamp member formed of a resilient semi-rigid material and having an inside diameter to fit snugly over said air fitting, wherein said C-shaped clamp member has a gap on one side dimensioned to permit the C-shaped clamp member to spread at said gap over an air fitting to snap on or snap off to one side; and leg means connected to said C-shaped clamp member and including means to receive said left and said right ribbons, respectively, thus securing said retaining device to the flange.

2. The retaining device of claim 1 wherein said leg means includes left and right leg members extending from opposite sides of said C-shaped clamp member.

3. The retaining device of claim 2 wherein said C-shaped clamp member and said leg members are unitarily formed of a resilient plastic resin.

4. The retaining device of claim 1 wherein the means to receive said left and said right ribbons includes a left slot and a right slot through which the respective ribbons pass.

5. The retaining device of claim 1 wherein said gap occupies about 60 degrees of arc.

6. The retaining device of claim 1 wherein said C-shaped clamp member has a smooth inner surface.

* * * * *